(12) United States Patent
Zheng et al.

(10) Patent No.: US 9,328,094 B2
(45) Date of Patent: May 3, 2016

(54) SUBSTITUTED BIARYL COMPOUNDS FOR LIGHT-EMITTING DEVICES

(71) Applicant: Nitto Denko Corporation, Ibaraki, Osaka (JP)

(72) Inventors: Shijun Zheng, San Diego, CA (US); David T. Sisk, San Diego, CA (US); Jensen Cayas, Bonita, CA (US)

(73) Assignee: NITTO DENKO CORPORATION, Osaka (JP)

( * ) Notice: Subject to any disclaimer, the term of this patent is extended or adjusted under 35 U.S.C. 154(b) by 544 days.

(21) Appl. No.: 13/622,197

(22) Filed: Sep. 18, 2012

(65) Prior Publication Data

US 2013/0075706 A1 Mar. 28, 2013

Related U.S. Application Data

(60) Provisional application No. 61/536,416, filed on Sep. 19, 2011.

(51) Int. Cl.
*C07D 401/14* (2006.01)
*C09K 11/06* (2006.01)
(Continued)

(52) U.S. Cl.
CPC ............ *C07D 401/14* (2013.01); *C07D 401/04* (2013.01); *C09K 11/06* (2013.01); *H01L 51/0067* (2013.01); *H01L 51/0072* (2013.01); *H05B 33/14* (2013.01); *C09K 2211/1014* (2013.01); *C09K 2211/1029* (2013.01);
(Continued)

(58) Field of Classification Search
CPC .... C07D 401/04; C07D 401/14; C09K 11/06; C09K 2211/1014; C09K 2211/1029; C09K 2211/1044; H01L 51/0067; H01L 51/0072; H01L 51/5012; H01L 51/5016; H01L 51/5036; H01L 51/5072; H05B 33/14
See application file for complete search history.

(56) References Cited

U.S. PATENT DOCUMENTS 5,766,779 A 6/1998 Shi et al.
6,541,490 B1 4/2003 Campbell et al.
(Continued)

FOREIGN PATENT DOCUMENTS

CN 101 219 989 7/2008
EP 0 825 803 2/1998
(Continued)

OTHER PUBLICATIONS

Translation for KR 10-2010-0075079 (publication date Jul. 2010).*
(Continued)

*Primary Examiner* — Dawn L. Garrett
(74) *Attorney, Agent, or Firm* — Knobbe, Martens, Olson & Bear, LLP

(57) ABSTRACT

Some substituted biaryl ring systems may be useful in light-emitting devices, such as those comprising a light-emitting diode. For example, substituted bipyridinyl or substituted phenylpyridinyl may be useful in these devices. The substituted biaryl ring system may have at least two different substituents, including one on each ring on the biaryl system. The first substituent may include optionally substituted carbazolyl, optionally substituted diphenylamine, optionally substituted diphenylaminophenyl, and optionally substituted carbazolylphenyl. The second substituent may include optionally substituted benzimidazol-2-yl, optionally substituted benzoxazol-2-yl, and an optionally substituted benzothiazol-2-yl.

20 Claims, 1 Drawing Sheet

| 35 |
|---|
| 30 |
| 25 |
| 20 |
| 15 |
| 10 |
| 5 |

(51) Int. Cl.
*H01L 51/54* (2006.01)
*H01L 51/00* (2006.01)
*H05B 33/14* (2006.01)
*C07D 401/04* (2006.01)
*H01L 51/50* (2006.01)

(52) U.S. Cl.
CPC ..... *C09K2211/1044* (2013.01); *H01L 51/5012* (2013.01); *H01L 51/5016* (2013.01); *H01L 51/5036* (2013.01); *H01L 51/5072* (2013.01)

(56) References Cited

U.S. PATENT DOCUMENTS

| | | | |
|---|---|---|---|
| 6,723,445 | B2 | 4/2004 | Li et al. |
| 6,916,555 | B2 | 7/2005 | Suzuki et al. |
| 7,579,353 | B2 | 8/2009 | Fiandor Roman et al. |
| 8,003,229 | B2 | 8/2011 | Sisk et al. |
| 8,057,921 | B2 | 11/2011 | Sisk et al. |
| 8,062,770 | B2 | 11/2011 | Sisk et al. |
| 8,062,771 | B2 | 11/2011 | Sisk et al. |
| 8,062,772 | B2 | 11/2011 | Sisk et al. |
| 8,062,773 | B2 | 11/2011 | Sisk et al. |
| 8,263,238 | B2 | 9/2012 | Sisk et al. |
| 8,585,926 | B2 | 11/2013 | Zheng |
| 8,952,364 | B2 | 2/2015 | Lai et al. |
| 9,172,051 | B2 * | 10/2015 | Zheng ............... H01L 51/006 |
| 2002/0024293 | A1 | 2/2002 | Igarashi et al. |
| 2002/0034656 | A1 | 3/2002 | Thompson et al. |
| 2003/0072964 | A1 | 4/2003 | Kwong et al. |
| 2003/0124381 | A1 | 7/2003 | Thompson et al. |
| 2003/0234608 | A1 * | 12/2003 | Lee et al. ............... 313/504 |
| 2004/0024293 | A1 | 2/2004 | Lawrence et al. |
| 2005/0127823 | A1 | 6/2005 | Iwakuma et al. |
| 2005/0271566 | A1 | 12/2005 | Yadav |
| 2006/0222886 | A1 | 10/2006 | Kwong et al. |
| 2007/0015006 | A1 | 1/2007 | Lee et al. |
| 2007/0075631 | A1 | 4/2007 | Tung et al. |
| 2007/0129613 | A1 | 6/2007 | Rochester et al. |
| 2008/0166591 | A1 | 7/2008 | Yamada et al. |
| 2009/0000658 | A1 | 1/2009 | Zakeeruddin et al. |
| 2009/0021146 | A1 | 1/2009 | Iida et al. |
| 2009/0134783 | A1 | 5/2009 | Lin et al. |
| 2009/0214921 | A1 | 8/2009 | Uensal et al. |
| 2009/0306385 | A1 | 12/2009 | Walters et al. |
| 2010/0060154 | A1 | 3/2010 | Nomura et al. |
| 2011/0196158 | A1 | 8/2011 | Zheng |
| 2011/0306922 | A1 | 12/2011 | Khan et al. |
| 2012/0179089 | A1 * | 7/2012 | Sisk et al. ............... 604/20 |
| 2012/0223635 | A1 * | 9/2012 | Mochizuki et al. ...... 313/512 |
| 2013/0069044 | A1 | 3/2013 | Ma et al. |
| 2014/0014883 | A1 | 1/2014 | Zheng et al. |
| 2014/0066627 | A1 | 3/2014 | Zheng et al. |

FOREIGN PATENT DOCUMENTS

| | | |
|---|---|---|
| EP | 1 857 521 | 11/2007 |
| EP | 1 858 094 | 11/2007 |
| JP | 2000-186066 | 7/2000 |
| JP | 2002-324678 | 11/2002 |
| JP | 2004-075603 | 3/2004 |
| JP | 2004-273190 | 9/2004 |
| JP | 2007-291092 | 11/2007 |
| JP | 2008-115131 | 5/2008 |
| JP | 2008-120696 | 5/2008 |
| JP | 2008-133225 | 6/2008 |
| JP | 2008-156266 | 7/2008 |
| JP | 2008-162910 | 7/2008 |
| JP | 2008-214306 | 9/2008 |
| JP | 2008-214307 | 9/2008 |
| JP | 2009-158848 | 7/2009 |
| JP | 2009-224763 | 10/2009 |
| JP | 2010-083862 | 4/2010 |
| JP | 2010-513971 | 4/2010 |
| KR | 10-2009-0073850 | 7/2009 |
| KR | 10-2009-0073852 | 7/2009 |
| KR | 10-2010-0075079 | * 7/2010 |
| WO | WO 03/078541 | 9/2003 |
| WO | WO 2004/074399 | 9/2004 |
| WO | WO 2006/080229 | 8/2006 |
| WO | WO 2006/095539 | 9/2006 |
| WO | WO 2008/027132 | 3/2008 |
| WO | WO 2009/096549 | 8/2009 |
| WO | WO 2010/076991 | 7/2010 |
| WO | WO 2010/090925 | 8/2010 |
| WO | WO 2011/156414 | 12/2011 |

OTHER PUBLICATIONS

Billmeyer, et al., "Principles of Color Technology", 2nd edition, John Wiley & Sons, Inc., New York, 1981.
CIE 1971, International Commission on Illumination, Colorimetry: Official Recommendations of the International Commission on Illumination, Publication CIE No. 15 (E-1.3.1) 1971, Bureau Central de la CIE, Paris, 1971.
Gustafsson et al. "Flexible Light-Emitting Diodes Made from Soluble Conducting Polymer," Nature, Jun. 11, 1992, vol. 357, pp. 477-479.
Miao et al., "Crystal Structure of bis(3,3'-bis(1-ethyl-1H-benzimidazol-2-yl)-2,2'-bipyridine)Copper(II) Diperchlorate Monohydrate, [Cu(C28H24N6)2][ClO4]2•H2O", NCS 222, 2007, pp. 323-326.
Miao et al., "Synthesis and Crystal Structure of 3,3'-Bis(2-benzimidazolyl)-2,2'-dipyridine with Hydrated Zinc(II) Perchlorate", Chinese Journal of Structural Chemistry, 2007, vol. 26, No. 4, pp. 439-444.
Spillane et al., "The Dichotomy in the DNA-Binding Behaviour of Ruthenium(II) Complexes Bearing Benzoxazole and Benzothiazole Groups", Journal of Inorganic Biochemistry, 2008, vol. 102, pp. 673-683.
Stibrany, Robert Timothy, "Exploration of Benzimidazole Chemistry", Thesis, Rutgers University, New Jersey, 2008, pp. 3.
Adachi et al., "Nearly 100% Internal Phosphorescence Efficiency in an Organic Light-Emitting Device", Journal of Applied Physics, vol. 90, Issue 10, Nov. 15, 2001, pp. 5048-5051.
Baldo et al., "High-Efficiency Fluorescent Organic Light-Emitting Devices Using a Phosphorescent Sensitizer", Nature, vol. 403, Feb. 17, 2000, pp. 750-753.
Cai et al., "Electron and Hole Transport in a Wide Bandgap Organic Phosphine Oxide for Blue Electrphosphorescence", Applied Physics Letters, vol. 92, Feb. 28, 2008, pp. 3.
Chen et al., "White Organic Light-Emitting Devices with a Bipolar Transport Layer Between Blue Fluorescent and Orange Phosphorescent Emitting Layers", Applied Physics Letters, vol. 91, Jul. 11, 2007, pp. 3.
Cheng et al., "[6,6'-Bis(benzimidazol-2-yl-N3)-2,2'-bipyridine]dichlorocobalt(II)-Dimethylform-amide (1/2)", Acta Crystallographica Section C, 1997, vol. C53, pp. 1238-1240.
Cheng et al., "White Organic Light-Emitting Devices Using a Phosphorescent Sensitizer", Applied Physics Letters, vol. 82, No. 24, Jun. 16, 2003, pp. 3.
D'Andrade et al., "Efficient Organic Electrophosphorescent White-Light-Emitting Device With A Triple Doped Emissive Layer", Advanced Materials, Apr. 5, 2004, vol. 16, Issue 7, pp. 624-628.
D'Andrade et al., "White Light Emission Using Triplet Excimers in Electrophosphorescent Organic Light-Emitting Devices", Advanced Materials, Aug. 5, 2002, vol. 14, Issue 15, pp. 1032-1036.
D'Andrade et al., "White Organic Light-Emitting Devices for Solid-State Lighting", Advanced Materials, Sep. 16, 2004, vol. 16, Issue 18, pp. 1585-1595.
Guan et al., "The Host Materials Containing Carbazole and Oxadiazole Fragment for Red Triplet Emitter in Organic Light-Emitting Diodes", Science Direct, Organic Electronics 7, May 19, 2006, pp. 330-336.
Koene et al., "Asymmetric Triaryldiamines as Thermally Stable Hole Transporting Layers for Organic Light-Emitting Devices," Chemical Materials, 1998, vol. 10, pp. 2235-2250.

(56) References Cited

OTHER PUBLICATIONS

Kreimer-Birnbaum et al., "Modified Porphyrins, Chlorins, Phthalocyanines and Purpurins: Second-Generation Photosensitizers for Photodynamic Therapy", Semin Hematol, 1989, vol. 26, pp. 157-173.

Liu et al., "Π-Conjugated Aromatic Enynes as a Single-Emitting Component for White Electroluminescence", Journal of American Chemical Society, 2006, vol. 128, No. 17, pp. 5592-5593.

Pawar et al., Synthesis of Benzoxazolo-1,8- & 1,6-naphthapyridines, Benzoxazolylbenzo[*h*]qolnoline & 1,9-Bisbenzoxazolophenanthroline, Indian Journal of Chemistry, 1976, vol. 14B, pp. 375-376.

Seo et al., "Highly Efficient White Organic Light-Emitting Diodes Using Two Emitting Material for Three Primary Colors (Red, Green and Blue)", Applied Physics Letters, vol. 90, May 16, 2007, pp. 3.

Soler et al., "Photodynamic Therapy of Superficial Basal Cell Carcinoma with 5-Aminolevulinic Acid with Dimethylsulfoxide and Ethylendiaminetetraacetic Acid: A Comparison of Two Light Sources", Photochemistry and Photobiology, 2000, vol. 71, No. 6, pp. 724-729.

Spillane et al., "Benzothiazole Bipyridine Complexes of Ruthenium(II) with Cytotoxic Activity", Journal of Biological Inorganic Chemistry, 2007, vol. 12, No. 6, pp. 797-807.

Spillane et al., "Inert Benzothiazole Functionalised Ruthenium(II) Complexes; Potential DNA Hairpin Binding Agents", Dalton Transactions, 2006, vol. 25, pp. 3122-3123.

Su et al., "Pyridine-Containing Bipoloar Host Materials for Highly Efficient Blue Phosphorescent OLEDs", Chemical Materials, vol. 20, Feb. 12, 2008, pp. 1691-1693.

Sun et al., "Management of Singlet and Triplet Excitons for Efficient White Organic Light-Emitting Devices", Nature, Apr. 2006, vol. 440, pp. 908-912.

Wang et al., "2,5. Bis [4. (9H.9. Carbazolyl) phenyl] pyridine Synthesis and Characterization", Huaxue Shiji, 2008, vol. 30, No. 4, pp. 280-282.

Wu et al., "Highly Efficient White-Electrophosphorescent Devices Based on Polyfluorene Copolymers Containing Charge-Transporting Pendent Units", Journal of Materials Chemistry, 2007, vol. 17, pp. 167-173.

Yu et al., "Synthesis and Characterization of Poly(Benzobisoxazole)s and Poly(Benzobisthiazole)s with 2,2'-bipyridyl units in the Backbone", Macromolecules, 1998, vol. 31, No. 17, pp. 5639-5646.

Zhao et al., "Studies of Third-Order Optical Nonlinearities of Model Compounds Containing Benzothiazole, Benzimidazole, and Benzoxazole Units", Chemistry of Materials, 1990, vol. 2, pp. 670-678.

* cited by examiner

| 35 |
|----|
| 30 |
| 25 |
| 20 |
| 15 |
| 10 |
| 5  |

SUBSTITUTED BIARYL COMPOUNDS FOR LIGHT-EMITTING DEVICES

CROSS-REFERENCE TO RELATED APPLICATIONS

This application claims the benefit of priority to U.S. Provisional Application No. 61/536,416, filed Sep. 19, 2011, which is hereby incorporated by reference in its entirety.

BACKGROUND

1. Field

The embodiments relate to compounds such as substituted biaryl ring systems for use in electronic devices such as light-emitting devices.

2. Description of the Related Art

Organic light-emitting devices (OLEDs) have been widely developed for flat panel displays, and are rapidly moving toward solid state lighting (SSL) applications. Some believe that a white OLED device with greater than 1,500 μm, a color rendering index (CRI) greater than 70, and an operating time greater than 10,000 hours at 1,000 lm/w may be useful in SSL applications. In order to reduce the driving voltage of an OLED device and extend the operational lifetime, it may be helpful to develop new high performance electron transport materials.

SUMMARY

Some substituted biaryl ring systems may be useful in electronic devices, including light-emitting devices, such as those comprising a light-emitting diode. For example, substituted bipyridine or substituted phenylpyridine may be useful in these devices. When the biaryl ring system has at least an electron donating substituent on a first ring of the ring system, and at least an electron withdrawing substituent on a second ring of the ring system, the compound may be useful in light-emitting devices or light-emitting diodes. These compounds may also be useful in other devices which comprise electron-transport and/or electron-injection materials. Examples of electron donating substituents may at least include, but are not limited to, optionally substituted aryl amines such as an optionally substituted diphenyl amine or an optionally substituted carbazole, where the nitrogen attaches directly to the first ring amine, or an optionally substituted amine substituted phenyl such as optionally substituted diphenylaminophenyl. Other electron donating substituents may also be included. Examples of electron withdrawing substituents may at least include, but are not limited to, a bicyclic heteroaryl comprising N, O, or S. Other electron withdrawing substituents may also be included. These compounds may be useful in light-emitting diodes as host materials, electron-transport materials, electron-injecting materials, electron-injecting and electron-transport materials, hole-transport materials, and/or for materials intended for some other purpose.

For example, some embodiments relate to a compound represented by Formula 1:

Hcy$^1$-Py-Hcy$^2$ (Formula 1)

wherein Hcy$^1$ is selected from the group consisting of optionally substituted carbazolyl, optionally substituted diphenylamine, optionally substituted diphenylaminophenyl, and optionally substituted carbazolylphenyl; Py is optionally substituted 3,3'-bipyrindinyl or optionally substituted phenylpyridinyl; and Hcy$^2$ is selected from the group consisting of optionally substituted benzimidazol-2-yl, optionally substituted benzoxazol-2-yl, and an optionally substituted benzothiazol-2-yl.

Some embodiments provide an organic light-emitting device comprising an organic component comprising a light-emitting component and a compound described herein.

Some embodiments relate to a composition comprising a compound described herein. In some embodiments, the composition may be a first layer disposed between a second layer and a third layer, wherein the first layer is configured to transport electrons from the second layer to the third layer. In some embodiments, the composition may also further comprise a fluorescent compound or a phosphorescent compound.

Some embodiments relate to a composition comprising at least 10%, at least 20%, at least 50%, at least 80%, at least 90%, or at least 95%, up to about 100% by weight of a compound described herein.

Some embodiments related to a method of transporting electrons between layers comprising: disposing a composition comprising a compound described herein between a first layer and a second layer so that the composition is capable of transporting electrons from the first layer to the second layer; and providing an electrical potential difference between the first layer and the second layer.

BRIEF DESCRIPTION OF THE DRAWINGS

FIG. 1 is a schematic diagram of an embodiment of a device described herein.

DETAILED DESCRIPTION

Unless otherwise indicated, when a chemical structural feature such as alkyl or aryl is referred to as being "optionally substituted," it is meant that the feature may have no substituents (i.e. be unsubstituted) or may have one or more substituents. A feature that is "substituted" has one or more substituents. The term "substituent" has the ordinary meaning known to one of ordinary skill in the art. In some embodiments, the substituent may be an ordinary organic moiety known in the art, which may have a molecular weight (e.g. the sum of the atomic masses of the atoms of the substituent) of less than about 500 g/m, about 300 g/m, about 200 g/m, about 100 g/m, or about 50 g/m. In some embodiments, the substituent comprises: 0-30, 0-20, 0-10, or 0-5 carbon atoms; and 0-30, 0-20, 0-10, or 0-5 heteroatoms independently selected from: N, O, S, Si, F, Cl, Br, or I; provided that the substituent comprises at least one atom selected from: C, N, O, S, Si, F, Cl, Br, or I. Examples of substituents include, but are not limited to, alkyl, alkenyl, alkynyl, carbazolyl, aryl, diarylamino, heteroaryl, heteroalicyclyl, aralkyl, heteroaralkyl, (heteroalicyclyl)alkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

As used herein the term "aryl" has the ordinary meaning understood by a person of ordinary skill in the art. In some embodiments, the term "aryl" may include an aromatic ring or aromatic ring system such as phenyl, naphthyl, etc.

As used herein the term "alkyl" has the ordinary meaning generally understood in the art, and includes a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1\text{-}10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3\text{-}10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3\text{-}10}$ cycloalkyl, such as $C_3H_6$ (e.g. cyclopropyl), $C_4H_8$ (e.g. cyclobutyl isomers such as cyclobutyl, methylcyclopropyl, etc.), $C_5H_{10}$ (e.g. cyclopentyl isomers such as cyclopentyl, methylcyclobutyl, dimethylcyclopropyl, etc.) $C_6H_{12}$ (e.g. cyclohexyl isomers), $C_7H_{15}$ (e.g. cycloheptyl isomers), etc. and the like.

An expression such as "$C_{1\text{-}12}$" (e.g. "$C_{1\text{-}12}$ alkyl") refers to the number of carbon atoms in a moiety, and similar expressions have similar meanings.

As used herein, the term "haloalkyl" includes alkyl having one or more halo substituents (such as F, Cl, Br, or I). The term "fluoroalkyl" includes alkyl having one or more fluoro substituents. The term "perfluoroalkyl" includes fluoroalkyl wherein all hydrogen atom are replaced by fluoro such as —$CF_3$, —$C_2F_5$, —$C_3F_7$, —$C_4F_9$, etc.

The structures of some of the optionally substituted ring systems referred to herein are depicted below. These ring systems may be unsubstituted, as shown below, or a substituent may independently be in any position normally occupied by a hydrogen atom when the ring system is unsubstituted.

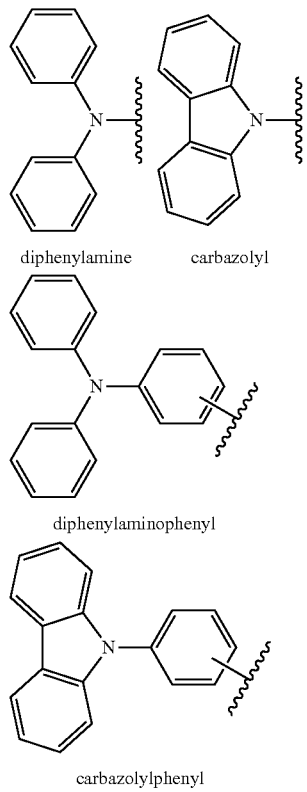

diphenylamine    carbazolyl diphenylaminophenyl carbazolylphenyl

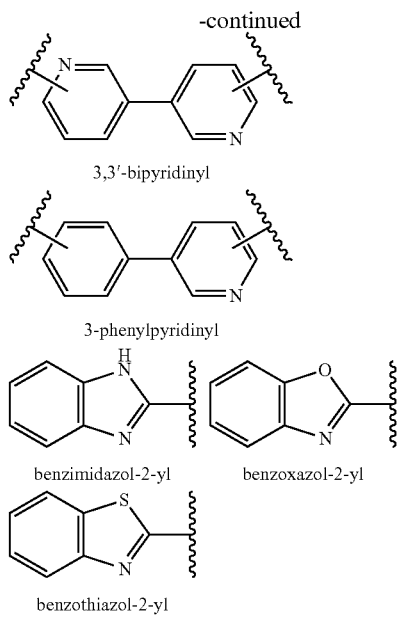

3,3'-bipyridinyl 3-phenylpyridinyl benzimidazol-2-yl    benzoxazol-2-yl benzothiazol-2-yl The term "low work function" has the ordinary meaning known to one of ordinary skill in the art. In some embodiments, a "work function" of a metal is a measure of the minimum energy required to extract an electron from the surface of the metal.

The term "high work function" has the ordinary meaning known to one of ordinary skill in the art, and may include a metal or alloy that easily injects holes and typically has a work function greater than or equal to about 4.5.

The term "low work function metal" has the ordinary meaning known to one of ordinary skill in the art, and may include a metal or alloy that easily loses electrons and typically has a work function less than about 4.3.

The expression "white light-emitting" has the ordinary meaning known to one of ordinary skill in the art, and may include a material is that emits white light. In some embodiments, white light may have the approximate CIE color coordinates (X=⅓, Y=⅓). The CIE color coordinates (X=⅓, Y=⅓) may be defined as the achromatic point. The X and Y color coordinates may be weights applied to the CIE primaries to match a color. A more detailed description of these terms may be found in CIE 1971, International Commission on Illumination, Colorimetry: Official Recommendations of the International Commission on Illumination, Publication CIE No. 15 (E-1.3.1) 1971, Bureau Central de la CIE, Paris, 1971 and in F. W. Billmeyer, Jr., M. Saltzman, Principles of Color Technology, 2nd edition, John Wiley & Sons, Inc., New York, 1981, both of which are hereby incorporated by reference in their entireties. The color rendering index (CRI) refers to the ability to render various colors and has values ranging from 0 to 100, with 100 being the best.

Some embodiments relate to compounds represented by at least one of Formula 1B, Formula 2, Formula 3, Formula 4, Formula 5, Formula 6, Formula 7, Formula 8, Formula 9, Formula 10, Formula 11, Formula 12, Formula 13, and/or Formula 14.

In some embodiments related to Formula 1, Hcy[1] and Hcy[2] may attach to different rings of Py. For example, if Py is bipyridinyl, Hcy[1] and Hcy[2] may attach to different pyridine rings of Py. Formula 2 is a non-limiting example of attaching Hcy[1] and Hcy[2] to different pyridine rings of a Py which is bipyridinyl. If Py is phenylpyridinyl, Hcy[1] may attach to the phenyl ring and Hcy² may attach to the pyridine ring. Formula 4 is a non-limiting example of attaching Hcy¹ to the phenyl ring and Hcy² to the pyridine ring of a Py which is phenylpyridinyl. Alternatively, if Py is phenylpyridinyl, Hcy¹ may attach to the pyridine ring and Hcy² may attach to the phenyl ring. Formula 2 is a non-limiting example of attaching Hcy¹ to the pyridine ring and Hcy² to the phenyl ring of a Py which is phenylpyridinyl.

Formula 1B

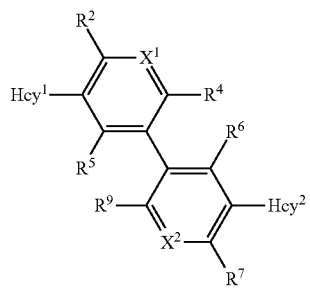

Formula 2

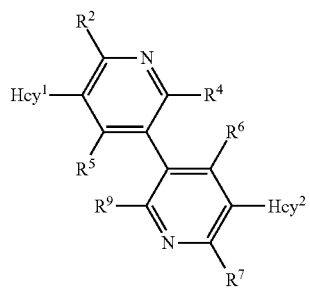

Formula 3

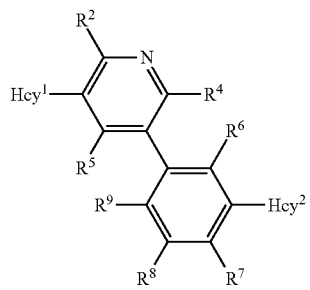

Formula 4

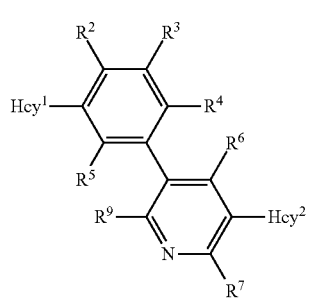

Formula 5

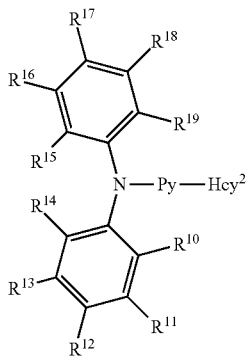

Formula 6

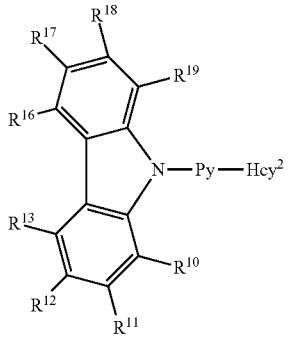

Formula 7

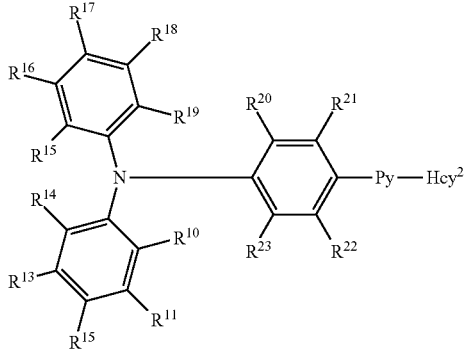

Formula 8

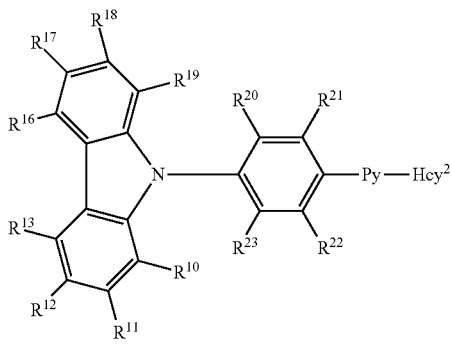

Formula 9

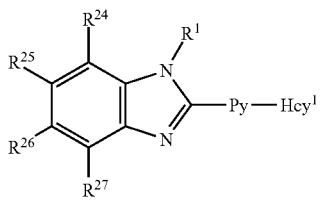

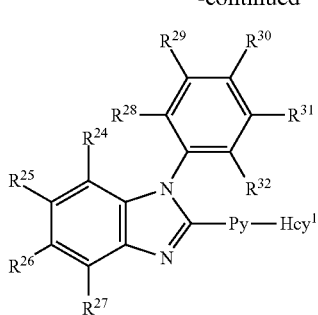

Formula 10

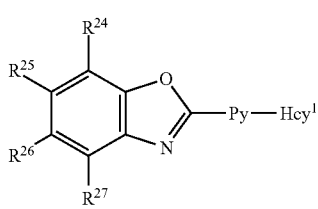

Formula 11

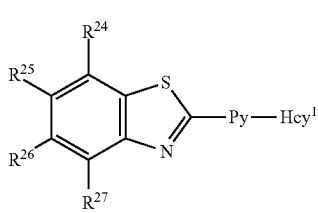

Formula 12

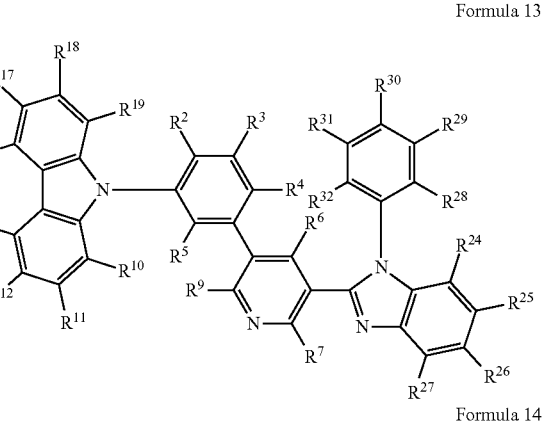

Formula 13

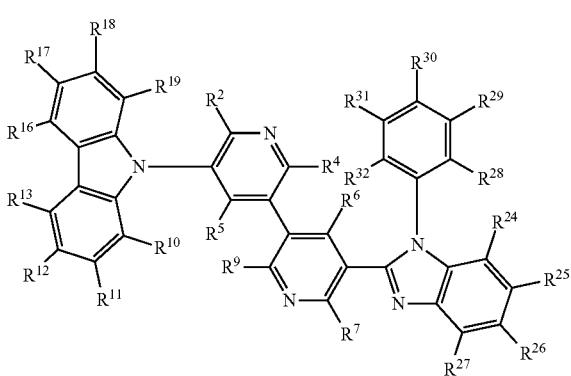

Formula 14

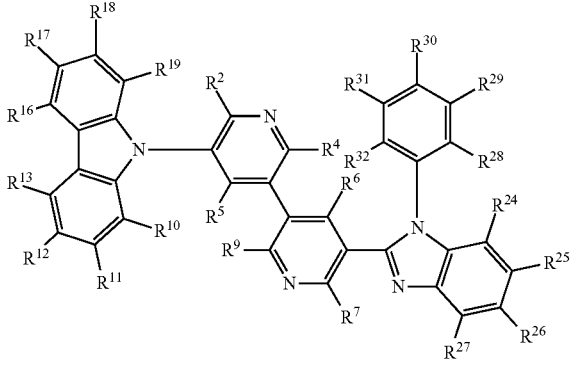

With respect to Formula 1B, $X^1$ may be N or C—$R^3$; and $X^2$ may be N or C—$R^8$.

With respect to any relevant formula above (including Formula 1), $Hcy^1$ may be selected from the group consisting of optionally substituted carbazolyl, optionally substituted diphenylamine, optionally substituted diphenylaminophenyl, and optionally substituted carbazolylphenyl. In some embodiments, $Hcy^1$ is unsubstituted, or has 1, 2, 3, 4, 5, 6, 7, or 8 substituents, such as any substituent described above. In some embodiments, $Hcy^1$ may be unsubstituted, or may have 1, 2, 3, 4, or 5 substituents independently selected from $CH_3$, $CH_2CH_3$, isopropyl, t-butyl, $CF_3$, F, Cl, Br, I, and $OCH_3$.

Also with respect to any relevant formula above, $Hcy^2$ may be selected from the group consisting of optionally substituted benzimidazol-2-yl, optionally substituted benzoxazol-2-yl, and optionally substituted benzothiazol-2-yl. In some embodiments, $Hcy^2$ is unsubstituted, or has 1, 2, 3, or 4 substituents, such as any substituent described above. In some embodiments, $Hcy^2$ may be unsubstituted, or may have 1, 2, or 3 substituents independently selected from $CH_3$, $CH_2CH_3$, isopropyl, t-butyl, $CF_3$, F, Cl, Br, I, and $OCH_3$.

Also with respect to any relevant formula above, Py may be optionally substituted 3,3'-bipyrindinyl or optionally substituted phenylpyridinyl. In some embodiments, Py is unsubstituted, or has 1, 2, 3, 4, 5, 6, or 7 substituents, such as any substituent described above. In some embodiments, Py may be unsubstituted, or may have 1, 2, or 3 substituents independently selected from $CH_3$, $CH_2CH_3$, isopropyl, t-butyl, $CF_3$, F, Cl, Br, I, and $OCH_3$.

Also with respect to any relevant formula above, $R^2$, $R^3$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ $R^{24}$, $R^{25}$, $R^{26}$, $R^{27}$, $R^{28}$, $R^{29}$, $R^{30}$, $R^{31}$, and $R^{32}$ may be any substituent. In some embodiments, any of $R^2$, $R^4$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ $R^{24}$, $R^{25}$, $R^{26}$, $R^{27}$, $R^{28}$, $R^{29}$, $R^{30}$, $R^{31}$, and $R^{32}$ may independently be F, Cl, Br, I, —CN, —CNO, —NCO, R', —OR', —COR', —$CO_2$R', —OCOR', —NR'COR'', CONR'R'', —NR'R'', wherein each R' and R'' is independently H; optionally substituted phenyl; $C_{1-12}$ alkyl such as methyl, ethyl, propyl isomers, cyclopropyl, butyl isomers, cyclobutyl isomers (such as cyclobutyl, methylcyclopropyl, etc.), pentyl isomers, cyclopentyl isomers, hexyl isomers, cyclohexyl isomers, heptyl isomers, cycloheptyl isomers, octyl isomers, cyclooctyl isomers, nonyl isomers, cyclononyl isomers, decyl isomers, cyclodecyl isomers, or the like; or $C_{1-6}$ alkyl.

In some embodiments related to Formula 2, at least one 1, at least 3, or all of: $R^2$, $R^4$, $R^5$, $R^6$, $R^7$, and $R^9$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 3, at least one 1, at least 4, or all of: $R^2$, $R^4$, $R^5$, $R^6$, $R^7$, $R^8$, and $R^9$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 4, at least one 1, at least 4, or all of: $R^2$, $R^3$, $R^4$, $R^5$, $R^6$, $R^7$, and $R^9$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 5, at least one 1, at least 4, at least 7, or all of: $R^{10}$, $R^{11}$, $R^{12}$, $R^{13}$, $R^{14}$, $R^{15}$, $R^{16}$, $R^{17}$, $R^{18}$, and $R^{19}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 6, at least one 1, at least 4, or all of: $R^{10}$, $R^{11}$, $R^{12}$, $R^{13}$, $R^{16}$, $R^{17}$, $R^{18}$, and $R^{19}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 7, at least one 1, at least 4, at least 8, at least 10, or all of: $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 8, at least one 1, at least 4, or all of: $R^{10}$, $R^{11}$, $R^{12}$, $R^{13}$, $R^{16}$, $R^{17}$, $R^{18}$, $R^{19}$, $R^{20}$, $R^{21}$, $R^{22}$, and $R^{23}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

With respect to Formula 9, $R^1$ may be optionally substituted aryl, such as optionally substituted phenyl or naphthyl. In some embodiments related to Formula 9, at least 1, at least 2, or all of: $R^{24}$, $R^{25}$, $R^{26}$, and $R^{27}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 10, at least 1, at least 4, at least 6, or all of: $R^{24}$, $R^{25}$, $R^{26}$, $R^{27}$, $R^{28}$, $R^{29}$, $R^{30}$, $R^{31}$, and $R^{32}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 11, at least 1, at least 2, or all of: $R^{24}$, $R^{25}$, $R^{26}$, and $R^{27}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 12, at least 1, at least 2, or all of: $R^{24}$, $R^{25}$, $R^{26}$, and $R^{27}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 13, at least 1, at least 5, at least 10, at least 15, at least 20, or all of: $R^2$, $R^3$, $R^4$, $R^5$, $R^6$, $R^7$, $R^9$, $R^{10}$, $R^{11}$, $R^{12}$, $R^{13}$, $R^{16}$, $R^{17}$, $R^{18}$, $R^{19}$, $R^{24}$, $R^{25}$, $R^{26}$, $R^{27}$, $R^{28}$, $R^{29}$, $R^{30}$, $R^{31}$ and $R^{32}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 14, at least 1, at least 5, at least 10, at least 15, at least 20, or all of: $R^2$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{24}$, $R^{25}$, $R^{26}$, $R^{27}$, $R^{28}$, $R^{29}$, $R^{30}$, $R^{31}$ and $R^{32}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

Some embodiments provide optionally substituted 9-(3-(5-(1-phenyl-1H-benzo[d]imidazol-2-yl)pyridin-3-yl)phenyl)-9H-carbazole or optionally substituted 9-(5'-(1-phenyl-1H-benzo[d]imidazol-2-yl)-3,3'-bipyridin-5-yl)-9H-carbazole.

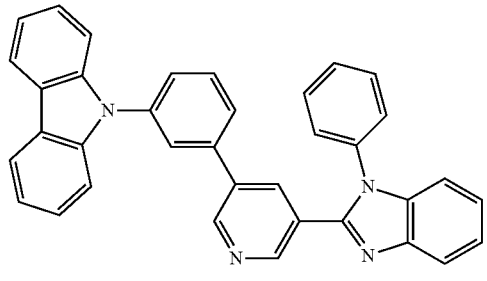

9-(3-(5-(1-phenyl-1H-benzo[d]imidazol-2-yl)pyridin-3-yl)phenyl)-9H-carbazole

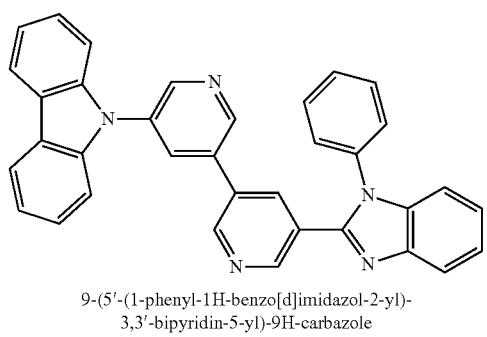

9-(5'-(1-phenyl-1H-benzo[d]imidazol-2-yl)-3,3'-bipyridin-5-yl)-9H-carbazole

The compounds and compositions described herein can be incorporated into light-emitting devices in various ways. For example, an embodiment provides an organic component disposed between an anode and a cathode. In some embodiments, the device is configured so that holes can be transferred from the anode to the organic component. In some embodiments, the device is configured so that electrons can be transferred from the cathode to the organic component. The organic component may comprise the compounds and/or compositions described herein.

An anode layer may comprise a conventional material such as a metal, a mixed metal, alloy, a metal oxide or a mixed-metal oxide, or a conductive polymer. Examples of suitable metals include the metals in Groups 10, Group 11, and Group 12 transition metals. If the anode layer is to be light-transmitting, mixed-metal oxides of Groups 12, Group 13, and Group 14 metals or alloys thereof, such as zinc oxide, tin oxide, indium zinc oxide (IZO) or indium-tin-oxide (ITO) may be used. The anode layer may include an organic material such as polyaniline, e.g., as described in "Flexible light-emitting diodes made from soluble conducting polymer," Nature, vol. 357, pp. 477-479 (11 Jun. 1992). Examples of suitable high work function metals include but are not limited to Au, Pt, indium-tin-oxide (ITO), or alloys thereof. In some embodiments, the anode layer can have a thickness in the range of about 1 nm to about 1000 nm.

A cathode layer may include a material having a lower work function than the anode layer. Examples of suitable materials for the cathode layer include those selected from alkali metals of Group 1, Group 2 metals, Group 11, Group 12, and Group 13 metals including rare earth elements, lanthanides and actinides, materials such as aluminum, indium, calcium, barium, samarium and magnesium, and combinations thereof. Li-containing organometallic compounds, LiF, and Li₂O may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

In some embodiments, the organic component may comprise at least one light-emitting layer comprising a light-emitting component, and optionally, a host, such as a compound described herein, a hole-transport material, an electron-transport material, or an ambipolar material. In some embodiments, the device is configured so that holes can be transferred from the anode to the light-emitting layer. In some embodiments, the device is configured so that electrons can be transferred from the cathode to the light-emitting layer. If present, the amount of the host in a light-emitting layer can vary. In one embodiment, the amount of a host in a light-emitting layer is in the range of from about 1% to about 99.9% by weight of the light-emitting layer. In another embodiment, the amount of a host in a light-emitting layer is in the range of from about 90% to about 99% by weight of the light-emitting layer. In another embodiment, the amount of a host in a light-emitting layer is about 97% by weight of the light-emitting layer.

In some embodiments, the mass of the light-emitting component is about 0.1% to about 10%, about 1% to about 5%, or about 3% of the mass of the light-emitting layer. In some embodiments, the light-emitting layer may be a neat light-emitting layer, meaning that the light-emitting component is about 100% by weight of the light-emitting layer, or alternatively, the light-emitting layer consists essentially of light-emitting component. The light-emitting component may be a fluorescent and/or a phosphorescent compound. In some embodiments, the light-emitting component comprises a phosphorescent material.

The light-emitting component or compound may be chosen to vary the color of the light emitted by the light-emitting device. For example, a blue light-emitting component may emit a combination of visible photons so that the light appears to have a blue quality to an observer. In some embodiments, a blue light-emitting component may emit visible photons having an average wavelength in the range of about 440 nm or about 460 nm to about 490 nm or about 500 nm. The "average wavelength" of visible photons may include, when referring to the visible emission spectrum of a compound, the wavelength wherein the area under the curve for the part of the visible spectrum having a lower wavelength than the average wavelength is about equal to the area under the curve for the part of the visible spectrum having a higher wavelength than the average wavelength. Some non-limiting examples of compounds which may form part or all of a blue light-emitting component include iridium coordination compounds such as: bis-{2-[3,5-bis(trifluoromethyl)phenyl]pyridinato-N,C2'}iridium(III)-picolinate, bis(2-[4,6-difluorophenyl]pyridinato-N,C2')iridium(III) picolinate, bis(2-[4,6-difluorophenyl]pyridinato-N,C2')iridium(acetylacetonate), Iridium(III)bis(4,6-difluorophenylpyridinato)-3-(trifluoromethyl)-5-(pyridine-2-yl)-1,2,4-triazolate, Iridium(III)bis(4,6-difluorophenylpyridinato)-5-(pyridine-2-yl)-1H-tetrazolate, bis[2-(4,6-difluorophenyl)pyridinato-N,C²']iridium (III)tetra(1-pyrazolyl)borate, etc.

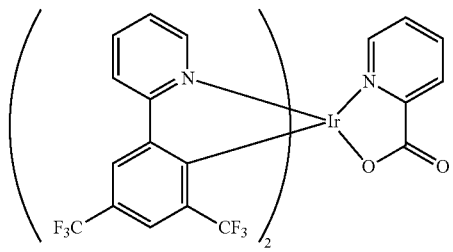

bis-{2-[3,5-bis(trifluoromethyl)phenyl]pyridinato-N,C2'}iridium(III)-picolinate
(Ir(CF₃ppy)₂(Pic))

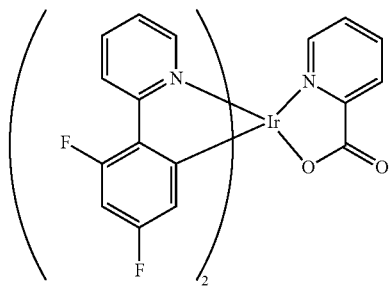

bis-(2-[4,6-difluorophenyl]pyridinato-N,C2')iridium(III) picolinate
[FIrPic]

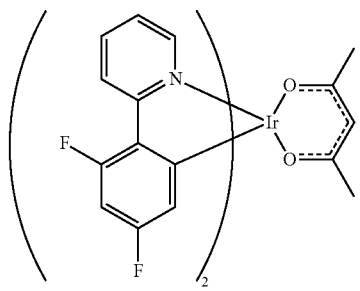

bis-(2-[4,6-difluorophenyl]pyridinato-N,C2')iridium(acetylacetonate)
[FIr(acac)]

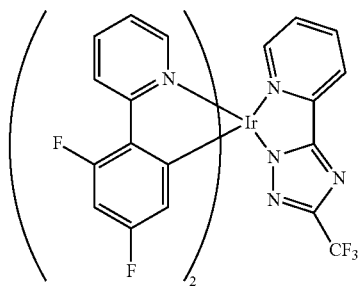

Iridium (III) bis(4,6-difluorophenylpyridinato)-3-(trifluoromethyl)-5-(pyridine-2-yl)-1,2,4-triazole
(FIrtaz)

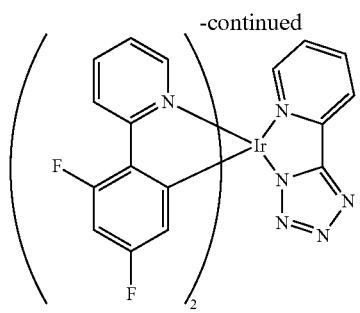

Iridium (III) bis(4,6-difluorophenylpyridinato)-5-(pyridine-2-yl)-1H-tetrazolate
(FIrN4)

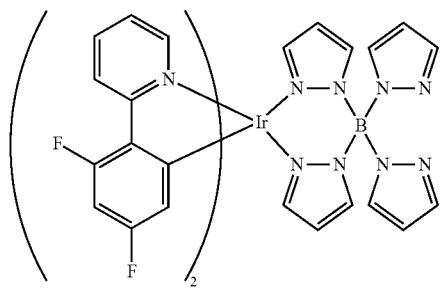

bis-(2-[4,6-difluorophenyl]pyridinato-N,C$^{2'}$)iridium(III)tetra(1-pyrazolyl)borate
(Fir6)

A red light-emitting component may emit a combination of visible photons so that the light appears to have a red quality to an observer. In some embodiments, a red light-emitting component may emit visible photons having an average wavelength in the range of about 600 nm or about 620 nm to about 780 nm or about 800 nm. Some non-limiting examples of compounds which may form part or all of a red light-emitting component include iridium coordination compounds such as: Bis[2-(2'-benzothienyl)-pyridinato-N,C3'] iridium(III)(acetylacetonate); Bis[(2-phenylquinolyl)-N, C2']iridium(III)(acetylacetonate); Bis[(1-phenylisoquinolinato-N,C2')]iridium(III)(acetylacetonate); Bis[(dibenzo[f,h]quinoxalino-N,C2')iridium(III)(acetylacetonate); Tris(2,5-bis-2-(9',9'-dihexylfluorene)pyridine)iridium(III); Tris[1-phenylisoquinolinato-N,C2']iridium(III); Tris-[2-(2'-benzothienyl)-pyridinato-N,C3']iridium(III); Tris[1-thiophen-2-ylisoquinolinato-N,C3']iridium(III); and Tris[1-(9,9-dimethyl-9H-fluoren-2-yl)isoquinolinato-(N,C3')iridium(III)), etc.

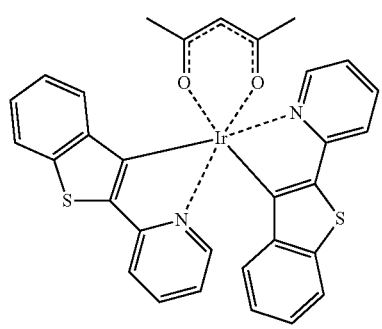

Ir(btp)$_2$(acac)

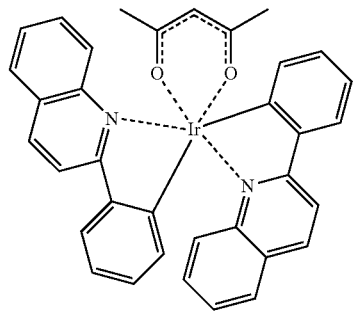

Ir(pq)$_2$(acac)

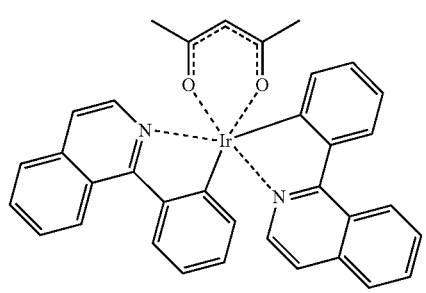

Ir(piq)$_2$(acac)

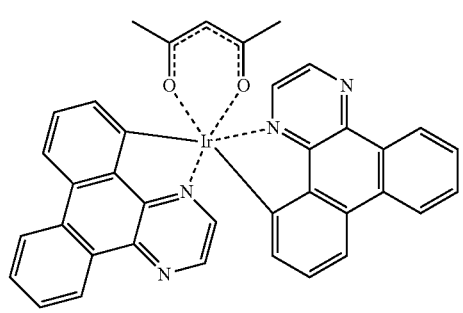

Ir(DBQ)$_2$(acac)

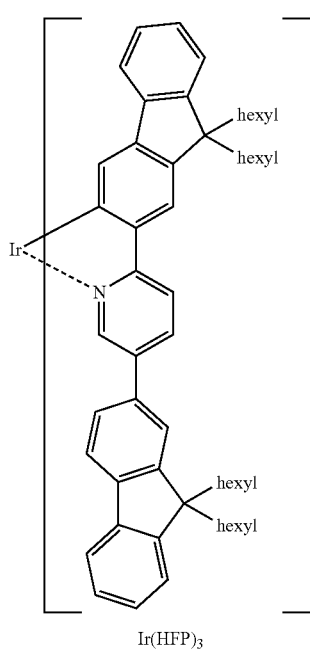

Ir(HFP)$_3$

-continued

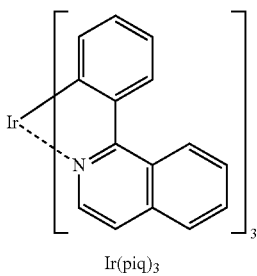
Ir(piq)₃

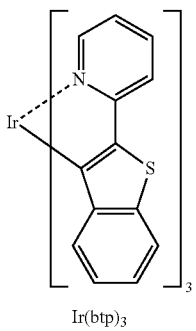
Ir(btp)₃

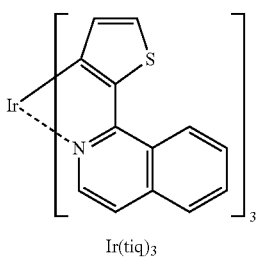
Ir(tiq)₃

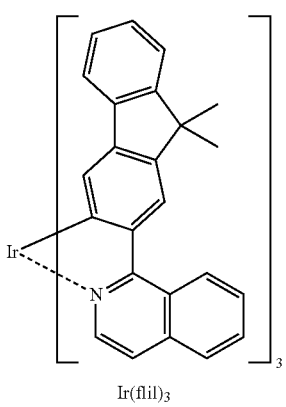
Ir(flil)₃

1. (Btp)₂Ir(III)(acac); Bis[2-(2'-benzothienyl)-pyridinato-N,C3']iridium(III)(acetylacetonate)
2. (Pq)₂Ir(III)(acac); Bis[(2-phenylquinolyl)-N,C2']iridium(III)(acetylacetonate)
3. (Piq)₂Ir(III)(acac); Bis[(1-phenylisoquinolinato-N,C2')]iridium(III)(acetylacetonate)
4. (DBQ)₂Ir(acac); Bis[(dibenzo[f,h]quinoxalino-N,C2')iridium(III)(acetylacetonate)
5. [Ir(HFP)₃], Tris(2,5-bis-2'-(9',9'-dihexylfluorene)pyridine)iridium(III)
6. Ir(piq)₃, Tris[1-phenylisoquinolinato-N,C2']iridium(III)
7. Ir(btp)₃, Tris-[2-(2'-benzothienyl)-pyridinato-N,C3']iridium(III)
8. Ir(tiq)₃, Tris[1-thiophen-2-ylisoquinolinato-N,C3']iridium(III)
9. Ir(fliq)₃; Tris[1-(9,9-dimethyl-9H-fluoren-2-yl)isoquinolinato-(N,C3') iridium(III))

A green light-emitting component may emit a combination of visible photons so that the light appears to have a green quality to an observer. In some embodiments, a green light-emitting component may emit visible photons having an average wavelength in the range of about 490 nm or about 500 nm to about 570 nm or about 600 nm. Some non-limiting examples of compounds which may form part or all of a green light-emitting component include iridium coordination compounds such as: Bis(2-phenylpyridinato-N,C2') iridium(III) (acetylacetonate)[Ir(ppy)₂(acac)], Bis(2-(4-tolyl)pyridinato-N,C2')iridium(III)(acetylacetonate)[Ir(mppy)₂(acac)], Bis(2-(4-tert-butyl)pyridinato-N,C2')iridium(III) (acetylacetonate)[Ir(t-Buppy)₂(acac)], Tris(2-phenylpyridinato-N,C2')iridium(III)[Ir(ppy)₃], Bis(2-phenyloxazolinato-N,C2')iridium(III)(acetylacetonate)[Ir(op)₂(acac)], Tris(2-(4-tolyl)pyridinato-N,C2')iridium(III)[Ir(mppy)₃], etc.

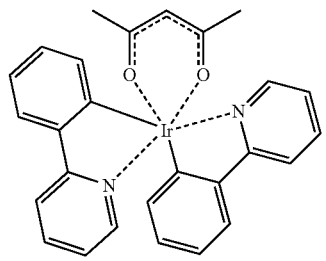
Ir(ppy)₂(acac)

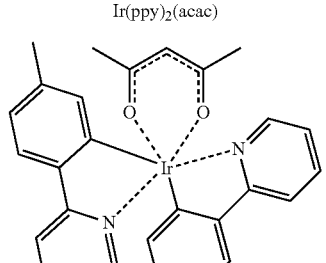
Ir(mppy)₂(acac)

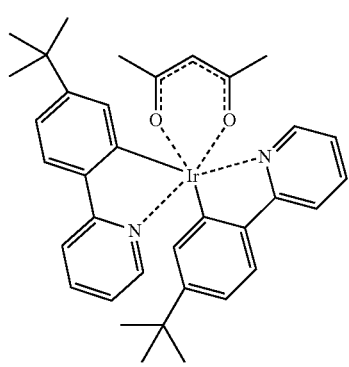
Ir(t-Buppy)₂(acac)

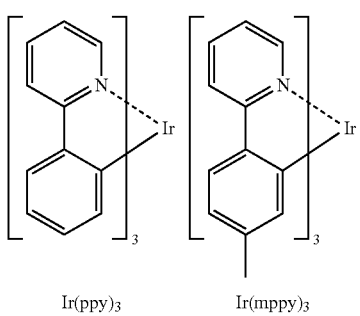

Ir(ppy)₃   Ir(mppy)₃

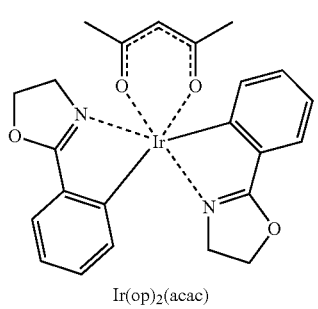

Ir(op)₂(acac)

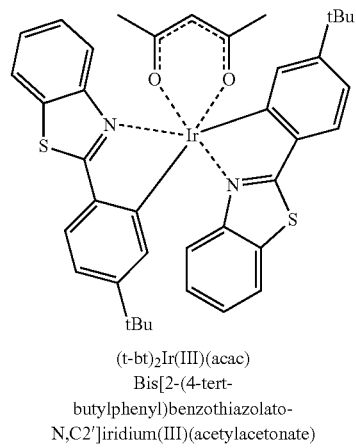

(t-bt)₂Ir(III)(acac)
Bis[2-(4-tert-
butylphenyl)benzothiazolato-
N,C2']iridium(III)(acetylacetonate)

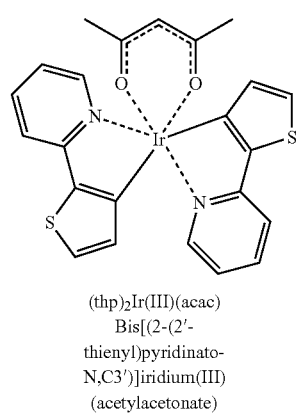

(thp)₂Ir(III)(acac)
Bis[(2-(2'-
thienyl)pyridinato-
N,C3')]iridium(III)
(acetylacetonate)

An orange light-emitting component may emit a combination of visible photons so that the light appears to have an orange quality to an observer. In some embodiments, an orange light-emitting component may emit visible photons having an average wavelength in the range of about 570 nm or about 585 nm to about 620 nm or about 650 nm. Some non-limiting examples of compounds which may form part or all of an orange light-emitting component include iridium coordination compounds such as: Bis[2-phenylbenzothiazolato-N,C2']iridium(III)(acetylacetonate), Bis[2-(4-tert-butylphenyl)benzothiazolato-N,C2']iridium(III)(acetylacetonate), Bis[(2-(2'-thienyl)pyridinato-N,C3')]iridium(III)(acetylacetonate), Tris[2-(9.9-dimethylfluoren-2-yl)pyridinato-(N,C3')]iridium(III), Tris[2-(9.9-dimethylfluoren-2-yl)pyridinato-(N,C3')]iridium(III), Bis[5-trifluoromethyl-2-[3-(N-phenylcarbzolyl)pyridinato-N,C2']iridium(III)(acetylacetonate), (2-PhPyCz)₂Ir(III)(acac), etc.

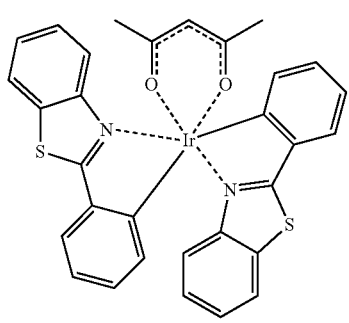

(bt)₂Ir(III)(acac)
Bis[2-
phenylbenzothiazolato-
N,C2'] iridium
(III)(acetylacetonate)

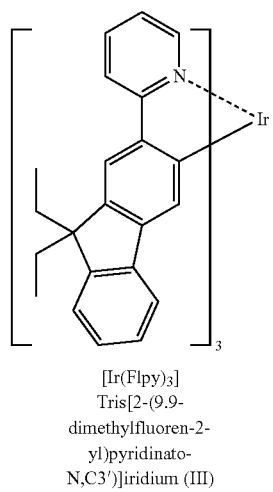

[Ir(Flpy)₃]
Tris[2-(9.9-
dimethylfluoren-2-
yl)pyridinato-
N,C3')]iridium (III)

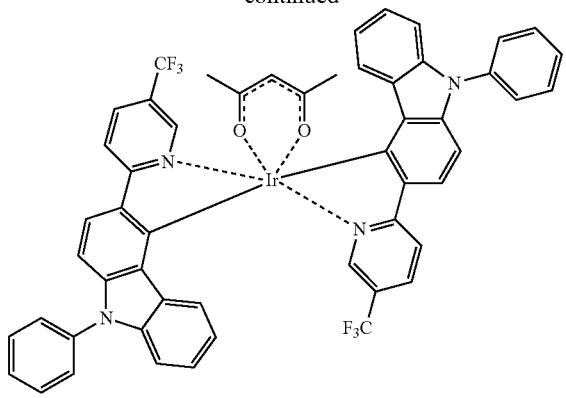

(Cz—CF₃)Ir(III)(acac)
Bis[5-trifluoromethyl-2-[3-(N-phenylcarbzolyl)pyridinato-N,C2'] iridium(III)(acetylacetonate)

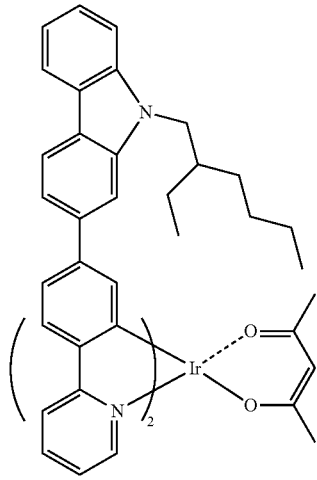

(2-PhPyCz)₂Ir(III)(acac)

The thickness of a light-emitting layer may vary. In one embodiment, a light-emitting layer has a thickness in the range of from about 1 nm to about 150 nm or about 200 nm.

In some embodiments, the light-emitting device may emit white light. A light-emitting layer may be configured to emit white light by including a white light emitter, or a combination of colored emitters which have a combined emission that appears white. Alternatively, a combination of different colored light-emitting layers may be configured to emit white light.

In some embodiments, the organic component may further comprise a hole-transport layer disposed between the anode and the light-emitting layer. The hole-transport layer may comprise at least one hole-transport material. In some embodiments, the hole-transport material comprises at least one of an aromatic-substituted amine, a carbazole, a polyvinylcarbazole (PVK), e.g. poly(9-vinylcarbazole); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; an oxadiazole; copper phthalocyanine; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4"-tris(3-methylphenylphenylamino)triphenylamine (MTDATA); N,N'-bis(3-methylphenyl)N,N'-diphenyl-[1,1'-biphenyl]-4,4'-diamine (TPD); 4,4'-bis[N-(naphthyl)-N-phenyl-amino]biphenyl (α-NPD); 4,4',4"-tris(carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); Bis[4-(p,p'-ditolyl-amino)phenyl]diphenylsilane (DTASi); 2,2'-bis(4-carbazolylphenyl)-1,1'-biphenyl (4CzPBP); N,N'N"-1,3,5-tricarbazoloylbenzene (tCP); N,N'-bis(4-butylphenyl)-N,N'-bis(phenyl)benzidine; or the like.

In some embodiments, the organic component may further comprise an electron-transport layer disposed between the cathode and the light-emitting layer. In some embodiments, the electron-transport layer may comprise a compound described herein. Other electron-transport materials may be included, such as 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ),2,9-dimethyl-4,7-diphenyl-phenanthroline (bathocuproine or BCP); and 1,3,5-tris[2-N-phenylbenzimidazol-z-yl]benzene (TPBI). In one embodiment, the electron transport layer is aluminum quinolate (Alq₃), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

If desired, additional layers may be included in the light-emitting device. These additional layers may include an electron injection layer (EIL), a hole-blocking layer (HBL), an exciton-blocking layer (EBL), and/or a hole-injection layer (HIL). In addition to separate layers, some of these materials may be combined into a single layer.

In some embodiments, the light-emitting device can include an electron-injection layer between the cathode layer and the light-emitting layer. In some embodiments, the electron-injection layer may comprise a compound described herein. Other suitable electron injection materials may also be included, and are known to those skilled in the art. Examples of suitable material(s) that can be included in the electron injection layer include but are not limited to, an optionally substituted compound selected from the following: aluminum quinolate (Alq₃), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate)aluminum, and a metal thioxinoid compound such as bis(8-quinolinethiolato) zinc. In one embodiment, the electron injection layer is aluminum quinolate (Alq₃), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof. In some embodiments, the electron-injection layer may be combined with an electron-transport layer and may comprise a compound described herein.

In some embodiments, the device can include a hole-blocking layer, e.g., between the cathode and the light-emitting layer. Various suitable hole-blocking materials that can be included in the hole-blocking layer are known to those skilled in the art. Suitable hole-blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton-blocking layer, e.g., between the light-emitting layer and the anode. In an embodiment, the band gap of the material(s) that comprise exciton-blocking layer is large enough to substantially prevent the diffusion of excitons. A number of suitable exciton-blocking materials that can be included in the exciton-blocking layer are known to those skilled in the art. Examples of material(s) that can compose an exciton-blocking layer include an optionally substituted compound selected from the following: aluminum quinolate (Alq₃), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole-injection layer, e.g., between the light-emitting layer and the anode. Various suitable hole-injection materials that can be included in the hole-injection layer are known to those skilled in the art. Exemplary hole-injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenylbenzidine, poly(N,N'-bis(4-butylphenyl)-N,N'-bis(phenyl)benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl)benzene, a polyacetylene derivative such as poly(1,2-bis-benzylthio-acetylene), and a phthalocyanine metal complex derivative such as phthalocyanine copper. In some embodiments, hole-injection materials, while still being able to transport holes, may have a hole mobility substantially less than the hole mobility of conventional hole transport materials.

Light-emitting devices comprising the compounds described herein can be fabricated using techniques known in the art, as informed by the guidance provided herein. For example, a glass substrate can be coated with a high work functioning metal such as ITO which can act as an anode. After patterning the anode layer, a hole-injection and/or hole-transport layer may be deposited on the anode in that order. A light-emitting layer that includes a light-emitting component, can be deposited on the anode, the hole-transport layer, or the hole-injection layer. The light-emitting layer may contain a compound described herein, and/or a compound described herein may be part of an electron-transport layer and/or an electron-injecting layer, deposited in that order, or may be part of an electron-injecting and electron-transport layer. The cathode layer, comprising a low work functioning metal (e.g., Mg:Ag), can then be deposited, e.g., by vapor deposition or sputtering. The device may also contain an exciton-blocking layer, an electron blocking layer, a hole blocking layer, a second light-emitting layer, or other layers that can be added to the device using suitable techniques.

In some embodiments, the OLED is made by a wet process such as a process that comprises at least one of spraying, spin coating, drop casting, inkjet printing, screen printing, etc. Some embodiments provide a composition which is a liquid suitable for deposition onto a substrate. The liquid may be a single phase, or may comprise one or more additional solid or liquid phases dispersed in it. The liquid typically comprises a light-emitting compound, a host material described herein and a solvent.

Example 1

HTH-1 was prepared as follows.

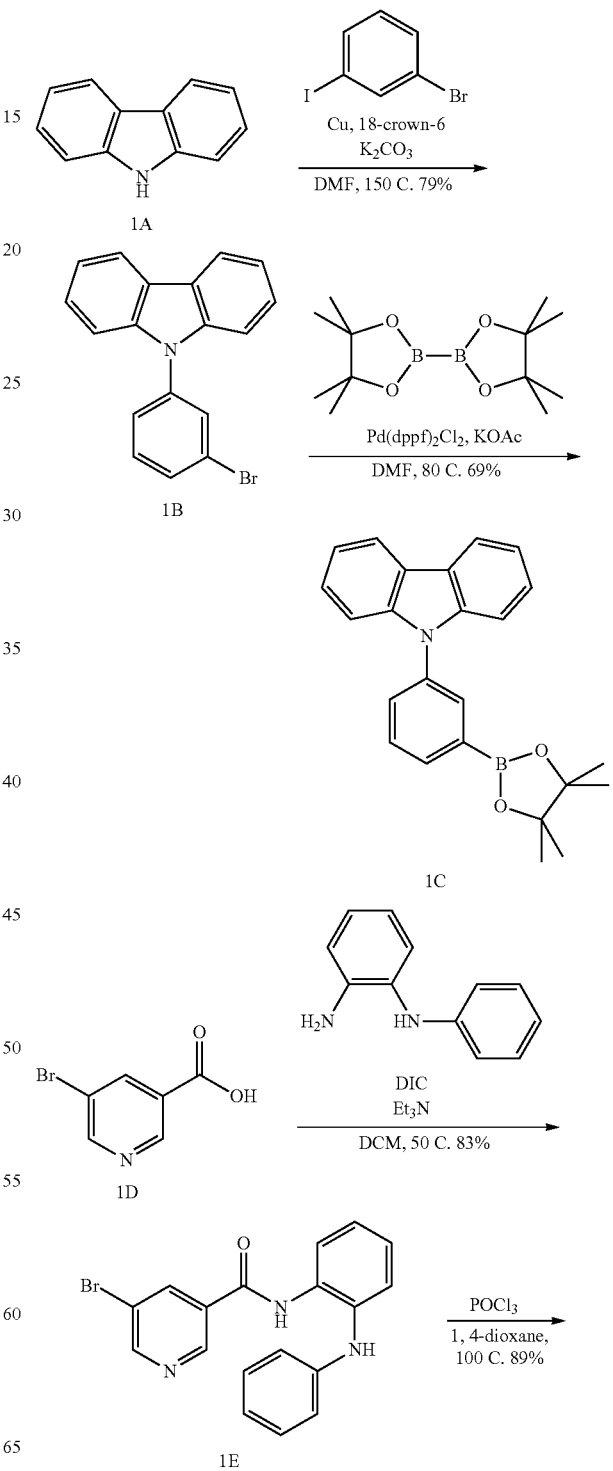

-continued

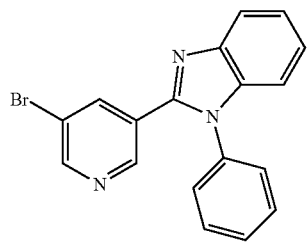

1F

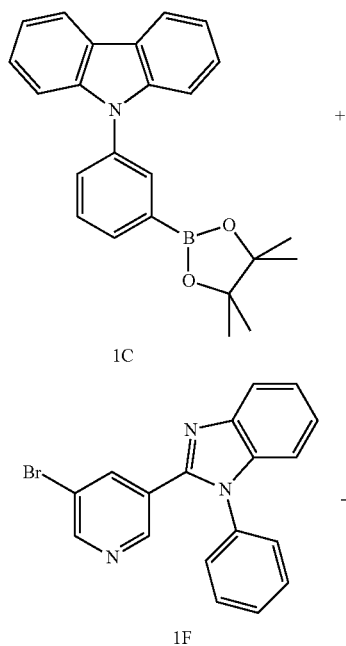

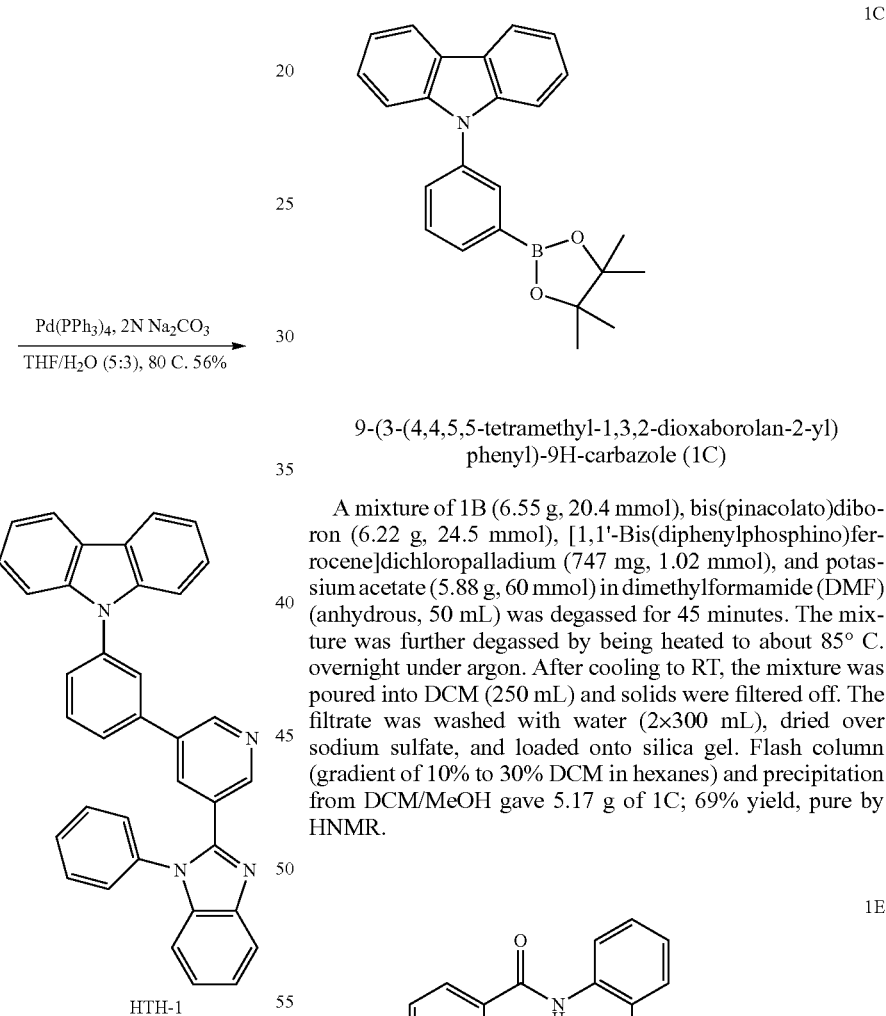

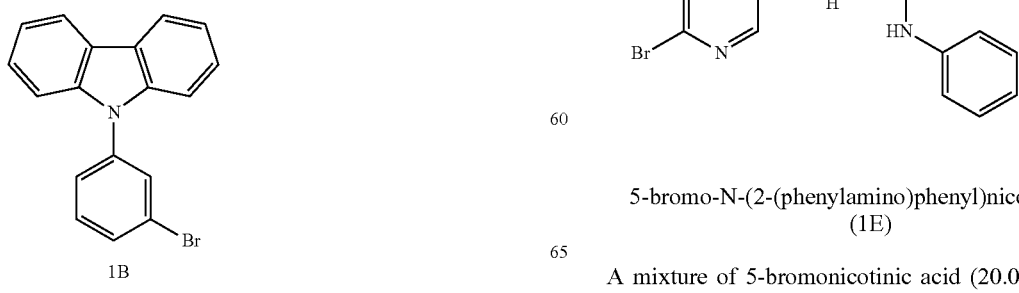

9-(3-bromophenyl)-9H-carbazole

A mixture of 9-H carbazole (4.0 g, 24.1 mmol), 3-bromoiodobenzene (10.23 g, 36.1 mmol), copper (3.06 g, 48.2 mmol), potassium carbonate (13.3 g, 96.4 mmol), 18-crown-6 (636 mg, 2.41 mmol) and DMF (anhydrous, 50 mL) was degassed for about 40 minutes. The mixture was then further degassed by heating to about 150° C. overnight under argon. After cooling to room temperature (RT), solids from reaction mixture were then filtered off. The filtrate was then poured into dichloromethane (DCM) (250 mL) and then washed with water (3×200 mL). The organic layer was dried over sodium sulfate and loaded onto silica gel. A flash column (hexanes) gave 6.56 g (79% yield) of product 1B; pure by HNMR.

9-(3-(4,4,5,5-tetramethyl-1,3,2-dioxaborolan-2-yl) phenyl)-9H-carbazole (1C)

A mixture of 1B (6.55 g, 20.4 mmol), bis(pinacolato)diboron (6.22 g, 24.5 mmol), [1,1'-Bis(diphenylphosphino)ferrocene]dichloropalladium (747 mg, 1.02 mmol), and potassium acetate (5.88 g, 60 mmol) in dimethylformamide (DMF) (anhydrous, 50 mL) was degassed for 45 minutes. The mixture was further degassed by being heated to about 85° C. overnight under argon. After cooling to RT, the mixture was poured into DCM (250 mL) and solids were filtered off. The filtrate was washed with water (2×300 mL), dried over sodium sulfate, and loaded onto silica gel. Flash column (gradient of 10% to 30% DCM in hexanes) and precipitation from DCM/MeOH gave 5.17 g of 1C; 69% yield, pure by HNMR.

5-bromo-N-(2-(phenylamino)phenyl)nicotinamide (1E)

A mixture of 5-bromonicotinic acid (20.0 g, 99 mmol), N-phenyl-o-phenylenediamine (19.32 g, 105 mmol), diisopropylcarbodiimide (DIC) (26.5 g, 210 mmol), and triethylamine (Et₃N)(2.65 g, 27 mmol) in DCM (anhydrous, 350 mL) was heated to about 50° C. and degassed overnight under argon. After cooling to RT, the solids were then filtered off. The filtrate was washed with water (2×200 mL), dried over sodium sulfate and loaded onto silica gel. A flash column (gradient of 3% to 10% ethyl acetate in DCM) gave 30.32 g of 1E; 83% yield, pure by HNMR.

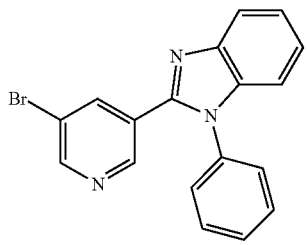

2-(5-bromopyridin-3-yl)-1-phenyl-1H-benzo[d]imidazole (1F)

Compound 1E (20.0 g, 54.3 mmol) was dissolved in 1,4-dioxane (anhydrous, 150 mL). Phosphorous oxychloride (36 g, 235 mmol) was then added dropwise. The resulting solution was heated at about 100° C. overnight; solids formed. After cooling to RT, the mixture was poured into hexanes (250 mL) to form additional precipitate. Solids were filtered then redissolved in DCM (200 mL) and washed with potassium carbonate (200 mL, saturated solution). The organic phase was collected, dried over sodium sulfate, and loaded onto silica gel. Short silica plug (20% ethyl acetate in hexanes and precipitation from hexanes gave 16.86 g of Compound 1F; 89% yield, pure by HNMR.

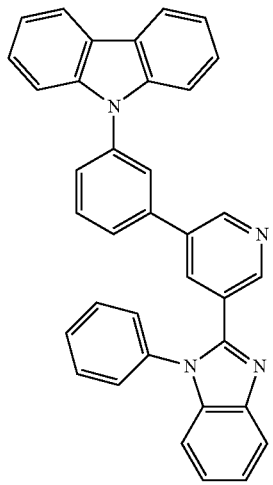

9-(3-(5-(1-phenyl-1H-benzo[d]imidazol-2-yl)pyridin-3-yl)phenyl)-9H-carbazole (HTH-1)

A mixture of compound 1C (3.0 g, 8.15 mmol), compound 1F (2.85 g, 8.15 mmol), tetrakistriphenylphosphine palladium (471 mg, 0.408 mmol), and sodium carbonate (3.09 g, 29.2 mmol) in tetrahydrofuran (THF)/water (50 mL/30 mL) was degassed for about 45 minutes. The mixture then heated to reflux (about 80° C.) overnight under argon. After cooling to RT, the reaction mixture was poured into DCM (300 mL) then washed with saturated sodium bicarbonate (200 mL), water (200 mL), and brine (200 mL). The organic phase was then collected, dried over magnesium sulfate, and loaded onto silica gel. A flash column (gradient of 25% to 40% ethyl acetate in DCM) and precipitation from ethyl acetate/methanol gave 2.34 g of HTH-1; 56% yield, pure by HNMR.

Example 2

HTH-2 was prepared as follows.

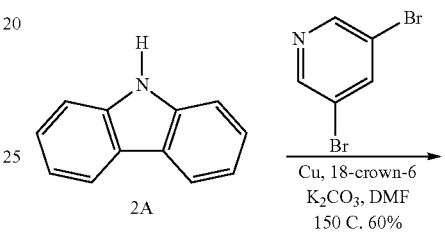

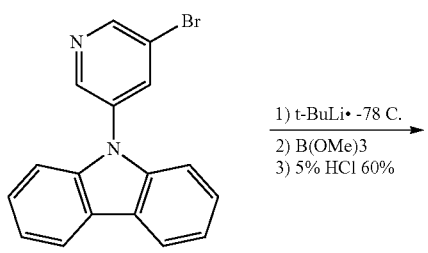

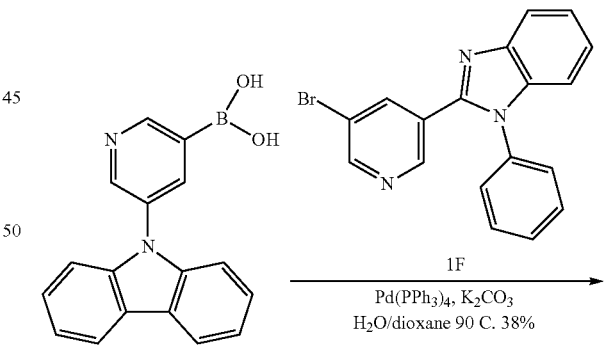

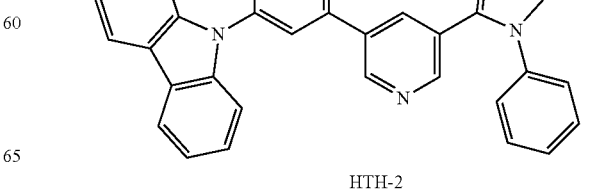

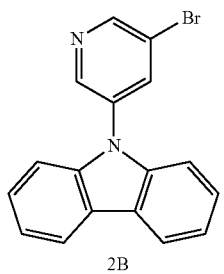

9-(5-bromopyridin-3-yl)-9H-carbazole (2B)

A mixture of 9H-carbazole (4.0 g, 24.1 mmol), 3,5-dibromopyridine (8.55 g, 36.1 mmol), copper powder (3.06 g, 48.2 mmol), potassium carbonate (13.3 g, 96.4 mmol) and 18-crown-6 (0.636 g, 2.4 mmol) in anhydrous DMF was degassed and heated at about 150° C. for about 40 hours. The crude mixture was then poured into water (200 mL), and then filtered. The solid was collected and dissolved in hot dichloromethane (500 mL) and an insoluble solid was then filtered off. The solution was absorbed on silica gel and purified by flash column (hexanes/ethyl acetate 12:1) to give a white solid product 2B (4.67 g, yield: 60%).

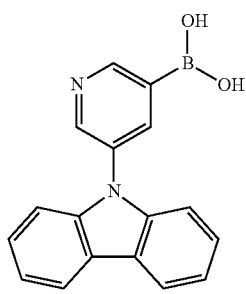

(5-(9H-carbazol-9-yl)pyridin-3-yl)boronic acid (2C)

To a solution of 9-(5-bromopyridin-3-yl)-9H-carbazole (2B) (1.7 g, 5.3 mmol) in THF (20 mL) was added a solution of tert-BuLi (1.7M in hexanes, 6.8 mL, 11.6 mmol) at about −78° C. The crude mixture was then stirred at about −78° C. for about 40 min, then a freshly distilled trimethylborate (0.89 mL, 8 mmol) was added. The resulting solution was stirred at RT overnight, then a 5% HCl aqueous solution (50 mL) was added and the whole was stirred for about 20 hours. The mixture was extracted with ethyl acetate (250 mL) three times, the organic phase was collected; dried over $Na_2SO_4$, concentrated and recrystallized with hexanes/dichloromethane to give product 2C, a light yellow solid (0.9 g, 60% yield).

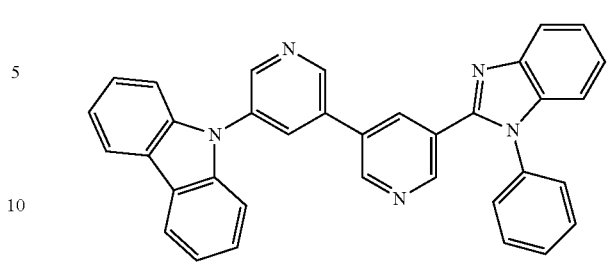

9-(5'-(1-phenyl-1H-benzo[d]imidazol-2-yl)-[3,3'-bipyridin]-5-yl)-9H-carbazole (HTH-2)

A mixture of (5-(9H-carbazol-9-yl)pyridin-3-yl)boronic acid (2C) (0.90 g, 3.1 mmol), 2-(5-bromopyridin-3-yl)-1-phenyl-1H-benzo[d]imidazole (1F) (0.856 g, 3.1 mmol), $Pd(PPh_3)_4$ (0.18 g, 0.155 mmol) and potassium carbonate (1.07 g, 7.8 mmol) in dioxane/water (20 mL/5 mL) was degassed and heated at about 90° C. overnight under argon atmosphere. The whole was poured into ethyl acetate (100 mL), then washed with brine (50 mL). The organic phase was collected and dried over $Na_2SO_4$, absorbed on silica gel, then purified by flash column (dichloromethane/methanol 40:1) to give a light yellow solid (0.78 g), which was purified again by flash column (silica gel, dichloromethane/methanol 50:1) followed by recrystallization in dichloromethane/methanol to give HTH-2, a light yellow solid (0.60 g, 38% yield).

Example 3

An exemplary configuration of the device comprising a compound described herein is shown in FIG. 1. The device comprises following layers in the order given: an ITO anode 5, a PEDOT hole-injection layer 10, a hole-transport layer 15, a first light-emitting layer 20, a second light-emitting layer 25, an electron-transport layer 30, and a LiF/Al cathode 35. The second light-emitting layer 25 comprises a compound described herein and a yellow or red light-emitting component.

Device Fabrication

Device A (HTH-2) was prepared as follows. Fabrication of light-emitting device: the ITO coated glass substrates were cleaned by ultrasound in de-ionized water, acetone, and consecutively in 2-propanol, baked at about 110° C. for about 3 hours, followed by treatment with UV-$O_3$ (oxygen plasma) for about 30 min. A layer of PEDOT: PSS (Baytron P purchased from H. C. Starck, Newton, Mass. or Euclid, Ohio, USA) was spin-coated at 6000 rpm onto the pre-cleaned and UV-O3 treated (ITO)-substrate and annealed at about 180° C. for about 30 min, yielding a thickness of around 20 nm. In a glove-box hosted vacuum deposition system at a pressure of $10^{-7}$ torr (1 torr=133.322 Pa), 4,4'4"-tri(N-carbazolyl)triphenylamine (TCTA) was first deposited on top of PEDOT/PSS layer at deposition rate of 0.1 nm/s, yielding about a 40 nm thick film. Then the blue emitter (FIrPic) with host of 5,5'-(dicarbazol-9-yl)-3,3'-bipyridine at 12% wt ratio was deposited on top of TCTA to form a 5 nm thick film, followed by deposition of HTH-2: Yellow-Emitter-1 (YE-1):Red-emitter (Ir(piq)$_2$acac), 3-co-deposition with the 5% wt for yellow and 0.5% wt for red, the total thickness of 5 nm, a 40 nm thick layer of 1,3,5-tris(N-phenylbenzimidizol-2-yl)benzene (TPBI), all at deposition rate around 0.1 nm/s. LiF and Al were then deposited successively at deposition rates of 0.005 and 0.2 nm/s, respectively.

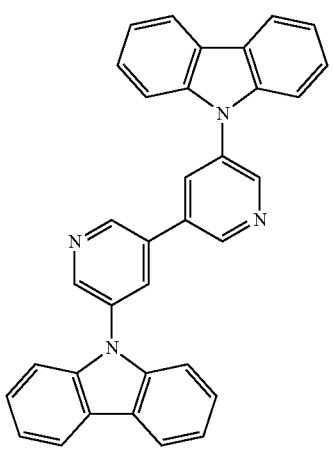

Host 5,5'-(dicarbazol-9-yl)-3,3'-bipyridine

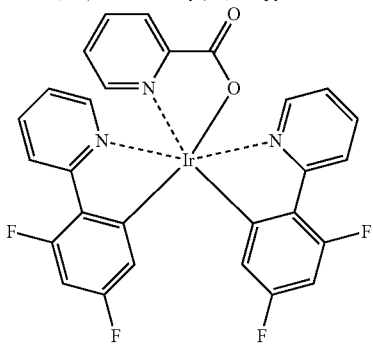

FirPic

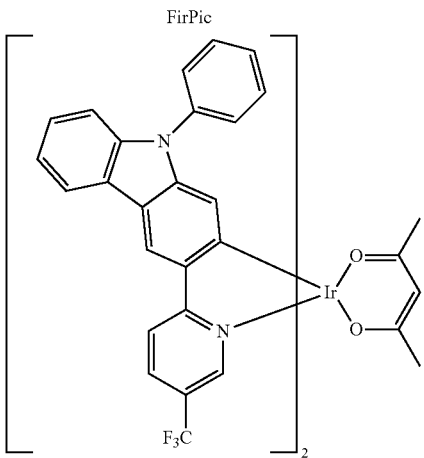

YE-1

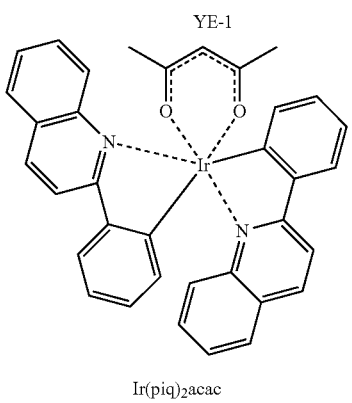

Ir(piq)₂acac

Device B (HTH-1) was made as set forth above except that HTH-1 was substituted for HTH-2. Device C (TPBI) was made as set forth above except that HTH-1 was substituted for HTH-2.

Table-1 shows device performance of using TPBI, HTH-1 and HTH-2 as the host in the second light-emitting layer. The Power Efficiency (lm/W) and Luminescent efficiency (cd/A) of the devices incorporating HTH-1 and/or HTH-2 exhibit comparable values to the device comprising TPBI at approximately the same operating voltage, demonstrating operation within desired device parameters.

TABLE 1

| Host | V @ 1000nit | CRI | PE (lm/W) | LE (cd/A) |
|---|---|---|---|---|
| TPBI | 3.9 | 70 | 50 | 62 |
| HTH-1 | 4 | 70.6 | 39 | 49 |
| HTH-2 | 3.8 | n/a | 34 | 39 |

Although the claims have been described in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A compound represented by Formula 1:

$$\text{Hcy}^1\text{-Py-Hcy}^2 \quad \quad \text{(Formula 1)}$$

wherein $Hcy^1$ is selected from the group consisting of optionally substituted carbazolyl, optionally substituted diphenylamine, optionally substituted diphenylaminophenyl, and optionally substituted carbazolylphenyl;

Py is optionally substituted 3,3'-bipyridinyl $Hcy^2$ is selected from the group consisting of optionally substituted benzimidazol-2-yl, optionally substituted benzoxazol-2-yl, and optionally substituted benzothiazol-2-yl;

$Hcy^1$ is in the 5 position of Py; and $Hcy^2$ is in the 5' position of Py.

2. The compound of claim 1, further represented by Formula 2:

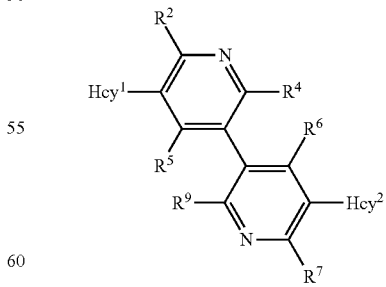

(Formula 2)

wherein $R^2$, $R^4$, $R^5$, $R^6$, $R^7$, and $R^9$ are independently selected from the group consisting of H, $C_{1-12}$ alkyl, and optionally substituted phenyl.

3. The compound of claim 2, wherein $R^2$, $R^4$, $R^5$, $R^6$, $R^7$, and $R^9$ are H.

4. The compound of claim 1, wherein Hcy¹ is selected from the group consisting of:

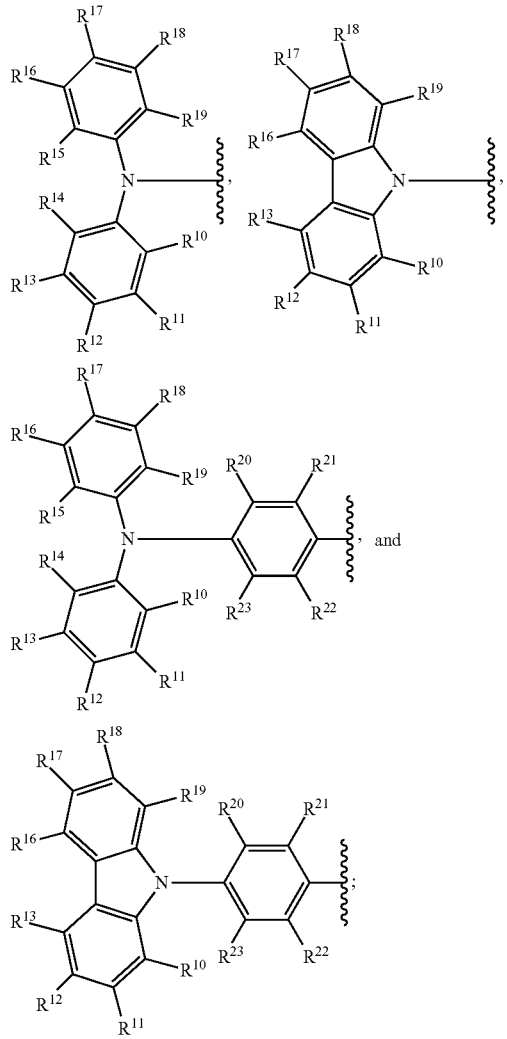

wherein $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ are independently selected from the group consisting of H, $C_{1-12}$ alkyl, and optionally substituted phenyl.

5. The compound of claim 4, wherein $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are H.

6. The compound of claim 4, wherein Hcy¹ is:

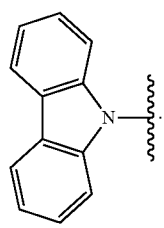 [SMILES: *n1c2ccccc2c2ccccc21 ; "."]

7. The compound of claim 1, wherein Hcy² is selected from the group consisting of:

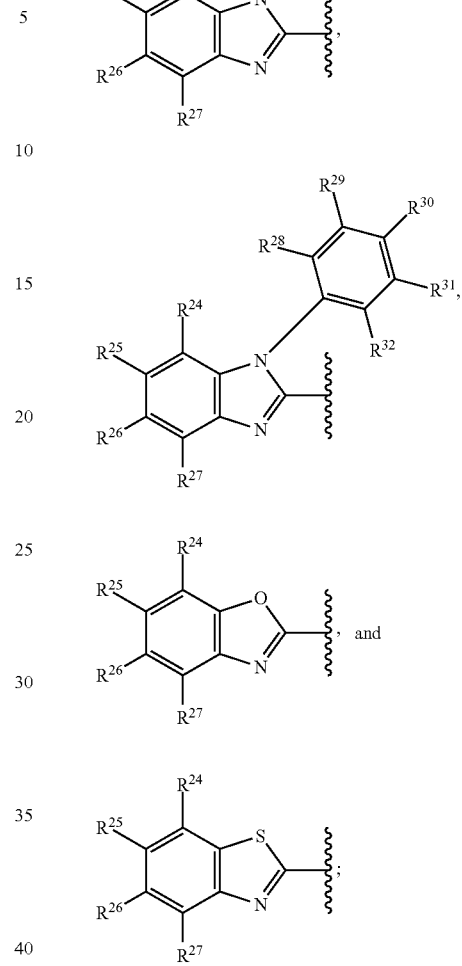

wherein $R_1$ is optionally substituted aryl; and
$R^{24}$, $R^{25}$, $R^{26}$, $R^{27}$, $R^{28}$, $R^{29}$, $R^{30}$, $R^{31}$, and $R^{32}$ are independently selected from the group consisting of H, $C_{1-12}$ alkyl, and optionally substituted phenyl.

8. The compound of claim 7, wherein $R^{24}$, $R^{25}$, $R^{26}$, $R^{27}$, $R^{28}$, $R^{29}$, $R^{30}$, $R^{31}$, and $R^{32}$ are H.

9. The compound of claim 7, wherein Hcy² is:

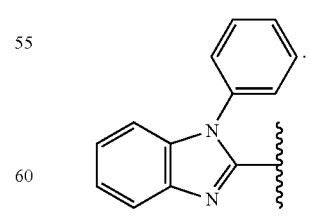

10. The compound of claim 1, wherein the compound is optionally substituted 9-(5'-(1-phenyl-1H-benzo[d]imidazol-2-yl)-3,3'-bipyridin-5-yl)-9H-carbazole.

11. The compound of claim 1, wherein the compound is:

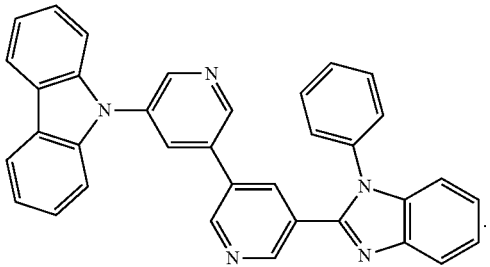 [SMILES: c1ccc(-n2c(-c3cncc(-c4cncc(-n5c6ccccc6c6ccccc65)c4)c3)nc3ccccc32)cc1]

12. An organic light-emitting device comprising an organic component comprising a light-emitting component and a compound of claim 1.

13. The device of claim 12, wherein the organic component further comprises a light-emitting layer comprising the light-emitting component.

14. The device of claim 13, wherein the organic component further comprises at least one layer comprising the compound, wherein the layer is configured to transport or inject electrons.

15. The device of claim 14, wherein the layer is an electron-transport layer, an electron-injecting layer, or an electron-injecting and electron-transport layer.

16. A composition comprising a compound of claim 1.

17. The composition of claim 16, further comprising a fluorescent compound or a phosphorescent compound.

18. The composition of claim 17, wherein the fluorescent compound or phosphorescent compound is selected from the group consisting of: bis-{2-[3,5-bis(trifluoromethyl)phenyl]pyridinato-N,C2'}iridium(III)-picolinate, bis(2-[4,6-difluorophenyl]pyridinato-N,C2')iridium (III) picolinate, bis(2-[4, 6-difluorophenyl]pyridinato-N, C2') iridium (acetylacetonate), Iridium (III) bis(4, 6-difluorophenylpyridinato)-3-(trifluoromethyl)-5-(pyridine-2-yl)-1,2,4-triazolate, Iridium (III) bis(4, 6-difluorophenylpyridinato)-5-(pyridine-2-yl)-1H-tetrazolate, bis[2-(4, 6-difluorophenyl)pyridinato-N, $C^{2'}$]iridium(III)tetra(1-pyrazolyl)borate, Bis[2-(2'-benzothienyl)-pyridinato-N,C3']iridium (III)(acetylacetonate); Bis[(2-phenylquinolyl)-N,C2']iridium (III) (acetylacetonate); Bis[(1-phenylisoquinolinato-N,C2')]iridium (III) (acetylacetonate); Bis[(dibenzo[f,h]quinoxalino-N,C2') iridium (III)(acetylacetonate); Tris(2, 5-bis-2'-(9',9'-dihexylfluorene)pyridine)iridium (III); Tris[1-phenylisoquinolinato-N,C2']iridium (III); Tris-[2-(2'-benzothienyl)-pyridinato-N,C3']iridium (III); Tris[1-thiophen-2-ylisoquinolinato-N,C3']iridium (III); and Tris[1-(9,9-dimethyl-9H-fluoren-2-yl)isoquinolinato-(N,C3') iridium (III)), Bis(2-phenylpyridinato-N, C2') iridium(III)(acetylacetonate) [Ir(ppy)₂(acac)], Bis(2-(4-tolyl)pyridinato-N, C2') iridium(III)(acetylacetonate) [Ir(mppy)₂(acac)], Bis(2-(4-tert-butyl)pyridinato-N,C2') iridium (III)(acetylacetonate) [Ir(t-Buppy)₂(acac)], Tris(2-phenylpyridinato-N,C2') iridium (III) [Ir(ppy)₃], Bis(2-phenyloxazolinato-N,C2')iridium (III) (acetylacetonate) [Ir(op)₂(acac)], Tris(2-(4-tolyl)pyridinato-N,C2') iridium(III) [Ir(mppy)₃], Bis[2-phenylbenzothiazolato-N,C2']iridium (III)(acetylacetonate), Bis[2-(4-tert-butylphenyl)benzothiazolato-N,C2' ]iridium(III) (acetylacetonate), Bis[(2-(2'-thienyl)pyridinato-N,C3')] iridium (III) (acetylacetonate), Tris[2-(9.9-dimethylfluoren-2-yl)pyridinato-(N,C3')]iridium (III), Tris[2-(9.9-dimethylfluoren-2-yl)pyridinato-(N,C3 ')]iridium (III), Bis[5-trifluoromethyl-2-[3-(N-phenylcarbzolyl)pyridinato-N, C2']iridium(III)(acetylacetonate), (2-PhPyCz)₂Ir(III)(acac), and combinations thereof.

19. A device comprising a first layer disposed between a second layer and a third layer, wherein the first layer comprises the composition of claim 16, wherein the first layer is configured to transport electrons from the second layer to the third layer.

20. A method of transporting electrons between layers comprising:
disposing a composition comprising a compound of claim 1 between a first layer and a second layer so that the composition is capable of transporting electrons from the first layer to the second layer; and
providing an electrical potential difference between the first layer and the second layer.

* * * * *